United States Patent [19]

Archer et al.

[11] Patent Number: 5,431,684

[45] Date of Patent: Jul. 11, 1995

[54] IMPLANTABLE DEFIBRILLATOR OUTPUT STAGE TEST CIRCUIT AND METHOD

[75] Inventors: Stephen T. Archer; Michael O. Williams, both of Sunnyvale, Calif.

[73] Assignee: Ventritex, Inc., Sunnyvale, Calif.

[21] Appl. No.: 172,510

[22] Filed: Dec. 22, 1993

[51] Int. Cl.[6] ............................................. A61N 1/36
[52] U.S. Cl. .................................................... 607/5
[58] Field of Search ..................... 607/5; 128/630, 897

[56] References Cited

U.S. PATENT DOCUMENTS

| | | | |
|---|---|---|---|
| 4,164,946 | 8/1979 | Langer | 128/419 |
| 5,111,816 | 5/1992 | Pless et al. | 128/419 |
| 5,163,428 | 11/1992 | Pless | 128/419 |
| 5,201,865 | 4/1993 | Kuehn | 128/419 |
| 5,224,475 | 7/1993 | Berg et al. | 128/419 |
| 5,275,158 | 1/1994 | Lopin | 128/419 |

FOREIGN PATENT DOCUMENTS 9316759 9/1993 WIPO ....................... 607/5

*Primary Examiner*—William E. Kamm
*Assistant Examiner*—Marianne Parker
*Attorney, Agent, or Firm*—Steven M. Mitchell; Mark J. Meltzer

[57] ABSTRACT

A method and apparatus for testing the integrity of biphasic and monophasic defibrillator switches in an implantable defibrillator without delivering a shock to the patient. The test circuitry is integrated with and implantable with the defibrillator and provides for the testing of the defibrillator switches without shocking the patient by charging the capacitive defibrillation voltage source to a predetermined level and discharging it through a resistive network and shunting one of the switches to provide an alternate current path to ground, while isolating the test circuitry from the patient. Switch conditions are capable of ascertainment by measuring residual charge, i.e., voltage, on the capacitive voltage source at selected measurement times.

20 Claims, 5 Drawing Sheets

IMPLANTABLE DEFIBRILLATOR OUTPUT STAGE TEST CIRCUIT AND METHOD

BACKGROUND OF THE INVENTION

This invention relates generally to implantable defibrillators and more particularly to implantable defibrillator test circuits and methods.

Defibrillators of many kinds are known. In general, defibrillators apply electric pulses or shocks to the heart of a patient to stop an on-going fibrillation activity of a patient's heart. The fibrillation involves the generation of uncoordinated electrical signals in the heart which prevent the normal functioning and pumping of the heart. In some instances, the defibrillator is implanted subcutaneously in the body of the patient. The patient may also have a need for a pacemaker, to supply the heart with regular or intermittent pulses at predetermined locations of the heart, in order to complement or induce its regular working operation. There are products in the medical electronics field which combine the functions of defibrillation and pacing.

Once such a device is implanted, the patient nonetheless does not become immune to cardiac difficulties. For one reason or other, despite the implantation of the defibrillator into the body of the patient, circumstances may arise which require the use of an external defibrillator. The voltages applied during defibrillation, whether by an implanted device or an external device are very high. An example of a typical voltage level employed by an implanted defibrillator during defibrillation is 750 volts. For defibrillation by an external device, voltages of several thousand volts may be applied. When such a high voltage pulse is applied to the chest of a patient from an external device, and the patient has an implanted defibrillator, substantial damage may result to the implanted defibrillator. Accordingly, it is considered prudent to test the implanted defibrillator prior to its next use. Of particular concern is the high voltage output stage of the implanted defibrillator and the switches which isolate the defibrillation electrodes on the heart from the high voltage capacitors which are used to deliver the electric shock to the patient's heart. These switches have been known to fuse shut or to become inoperable in an open position. In either case, the switches are rendered useless in the regular operation of the implanted defibrillator.

Many patents have been granted in the field of defibrillation arrangements. For example, U.S. Pat. No. 5,111,816 has been issued to Ventritex and its inventors Benjamin Pless, John G. Ryan, and James M. Culp on a combined defibrillator/pacemaker. The patent shows a system which is able to detect defibrillator lead breaks without delivering a defibrillation pulse to the patient. U.S. Pat. No. 4,164,946 has been granted to Alois A. Langer on the subject of fault detection in a permanently implanted cardioverter or defibrillator. The circuitry of the Langer patent includes built-in interrogation and testing and complex fibrillation detection circuitry used to monitor an ECG signal and to issue a fibrillation detection signal when predetermined characteristics are detected. A characteristic output signal is produced when the fibrillation detector circuit is functioning properly.

Another recent patent, U.S. Pat. No. 5,224,475 was granted to Berg et al. in 1993 on a method and apparatus for termination of ventricular tachycardia and ventricular fibrillation. According to this patent, an implantable defibrillator is provided with a plurality of defibrillation electrodes which may be reconfigured to define a plurality of defibrillation pathways. The device measures impedance along selected defibrillation pathways and monitors the success or failure of the pulse to accomplish defibrillation or cardioversion. The impedance paths are measured while electric current is applied to the heart of a patient. The teachings of this patent accordingly help optimize the correct positioning of electrodes in the body of a patient to ensure effective defibrillation can be accomplished. The impedance testing performed helps in the optimization process.

However, the patents indicated above are not specifically directed toward determination of the integrity of particular switching components in the defibrillation circuitry. These patents show approaches dealing with detection in lead breakage. They disclose complex arrangements to optimize the placement of defibrillation electrodes. The invention herein addresses something different.

In accordance with the invention, it is an object to ascertain the integrity of selected defibrillator components and switches to determine whether they are operating properly.

It is an object to test the circuitry of the defibrillator to determine whether any components are fused open or shut, thereby preventing their effective normal operation.

It is an object of the invention herein to conduct integrity testing without applying electric currents to or shocking the patient.

It is an object of the invention herein to inspect the condition of a defibrillator which is implanted in a patient without applying a defibrillation pulse to the patient.

It is further an object of the invention herein to detect the condition of implanted defibrillation circuitry without the use of fibrillation detection circuitry itself.

It is further an object of the invention herein to detect the condition of defibrillator circuitry with the use of the defibrillation circuitry normally used to implement defibrillation operation in a patient.

SUMMARY OF THE INVENTION

In particular, according to the invention herein, the high-voltage output stage of an implanted defibrillator or cardioverter is capable of evaluation as to particular components and switches. Evaluation of the output stage is enabled by incorporation of a self-test arrangement into the high-voltage output stage circuitry of the defibrillator. This high voltage circuitry used for defibrillation includes switches to isolate the defibrillation electrodes from ground and a potent capacitive source of high voltage charge. The defibrillation circuitry which can be tested in accordance with the invention herein includes circuitry for delivery of monophasic as well as biphasic defibrillation waveforms. The version of the invention which is directed toward testing a monophasic defibrillator is essentially directed toward the testing of the integrity of two switches, one of them opening and closing the ground connection (defined as the low end of the voltage source) and the other controlling the current path from high voltage to a positive defibrillation electrode.

The inventive self-test arrangement itself relies upon an arrangement of resistors connected to the output stage of an implantable defibrillator. The switches permit a high voltage pulse to be applied to the heart during defibrillation operation. During test operation, a test pulse is applied to the resistor arrangement itself to determine how much of the capacitive charge initially stored on the high voltage source will be drained off during predetermined periods of time. Different discharge rates will accompany states of the resistor arrangement in which the switches are operating normally and states in which one or both of the switches are locked open or fused shut.

According to the invention, a resistor is connected to a first switch leading to the high voltage source. The other end of the resistor is connected to a second switch which leads to ground. Finally, a second resistor is connected to ground which shunts the first resistor and the second switch and connects to the high side of the first resistor at its connection with the first switch. This approach connects the test circuitry of the invention according to a monophasic approach between first and second defibrillation leads which are coupled to the heart of the patient. The first resistor is preferably connected to a high voltage source through the first switch. The low voltage terminal of the first resistor is connected to ground through the second switch. The second resistor is a shunt resistor to ground which is connected in parallel with the resistor connecting the first and second defibrillation leads. If a test pulse of given charge is applied at the input of the first switch, when both the first and second switches are signaled to close and allow current to flow to ground, a certain amount of charge depletion on the capacitive voltage source is to be expected, depending upon the resistance seen by the voltage source. With both switches in good operating condition, a given current flow and charge depletion will be measurable on the voltage source. According to well known techniques, the voltage and charge state of the capacitive voltage source implanted in a patient is readily determinable.

If the first switch does not close as directed, there will be no discharge of the capacitive voltage source. If the second switch does not close as directed, then the resistance seen by the voltage source will be greater and the amount of charge dissipated and current flow will be less than the amounts measurable when the second switch is closed. Accordingly, the failure of the second switch is externally determinably by measuring the remaining voltage and charge on the voltage source after a given amount of time and noting that the voltage drop has not been as great as one would have expected had both of the switches closed as directed. Similarly, it is detectable if the first or second switches fuse in a closed position. If the first switch is directed to open and is fused closed, discharge of the voltage source will continue and will be detected. If the second switch remains closed when directed to open and the first switch is closed, the voltage source will discharge at a faster rate than expected.

In summary, the method and arrangement according to this invention permit the checking of the condition of key high voltage output switches of a defibrillator, without application of shocks to the heart of a patient. The defibrillation output stage circuitry, according to one version, includes a resistor connected between internal nodes connected to first and second switches respectively connected to a high voltage capacitive source and ground. The circuitry further includes a second resistor which provides an alternate path to ground which shunts the first resistor and the second switch to ground. By discharging the capacitive voltage source over given time periods, different voltage levels on the voltage source after expiration of the given time periods are indicative of different switch conditions, permitting convenient diagnosis of failed high voltage delivery switches, whether the switches are fused closed or simply fail to open or close at the appropriate times.

These and other advantages of the present invention will become apparent upon reading the following detailed descriptions and studying the various figures of the drawings.

DETAILED DESCRIPTION OF THE PREFERRED EMBODIMENTS

Figure 1:
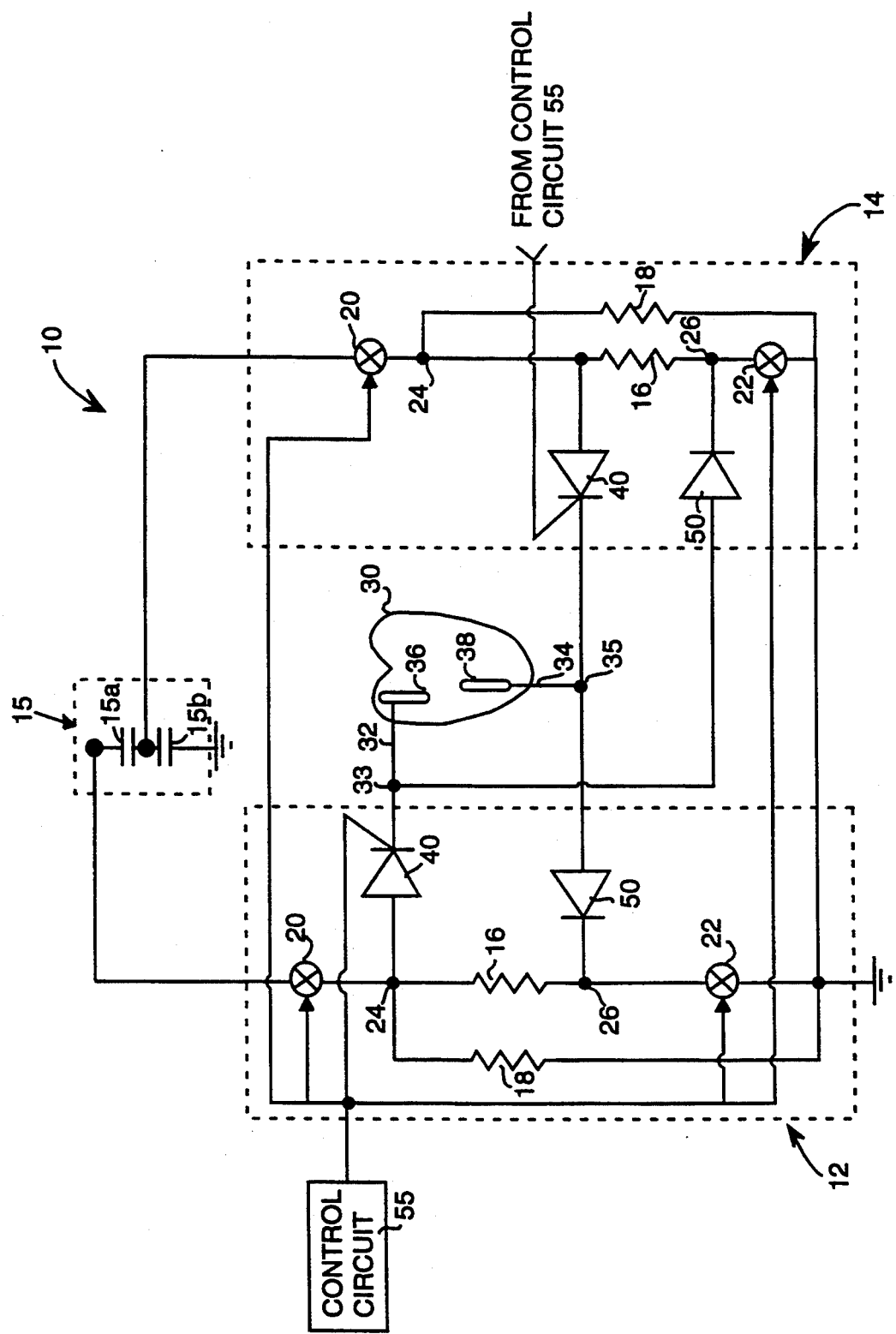
FIG. 1 shows a defibrillator output stage including an output stage test circuit according to the invention herein.

FIG. 1 shows a defibrillator output stage circuit 10 including first and second output stage subcircuits 12 and 14 connected to a preferably capacitive high voltage source 15. Defibrillator output stage circuit 10 is intended to deliver high voltage shocks to the heart upon microprocessor command. The circuitry of FIG. 1 is directed toward a biphasic version of the invention herein. As will be seen, defibrillation and testing of the integrity of defibrillation circuit components may be conducted in accordance with the invention according to monophasic or multiphasic approaches, the biphasic approach being a special case of the multiphasic approach.

Figure 2B:
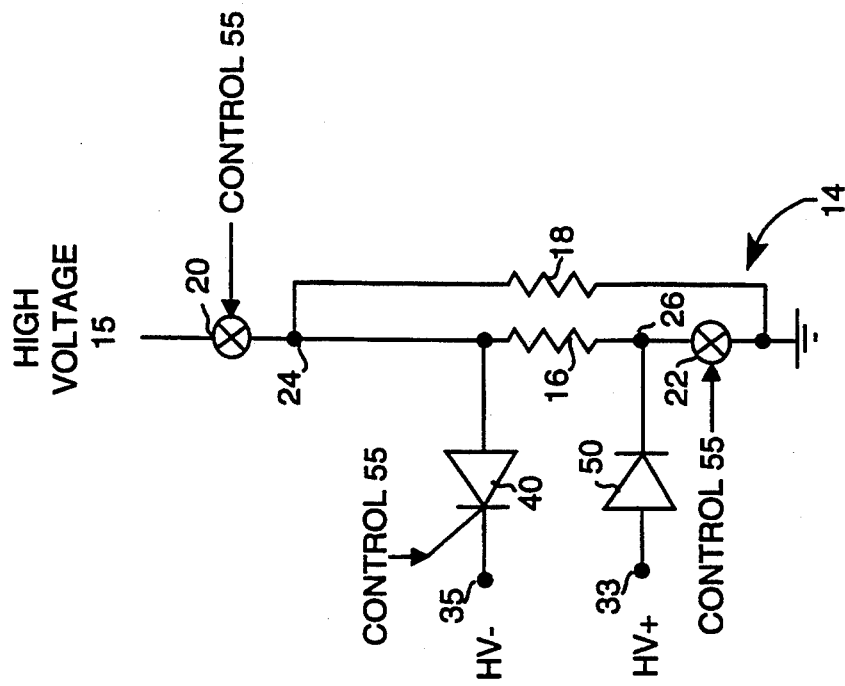
FIGS. 2a and 2b show selected portions of the output stage test circuit in FIG. 1, which apply to respective first and second phases of a biphasic defibrillation waveform.
Figure 2A:
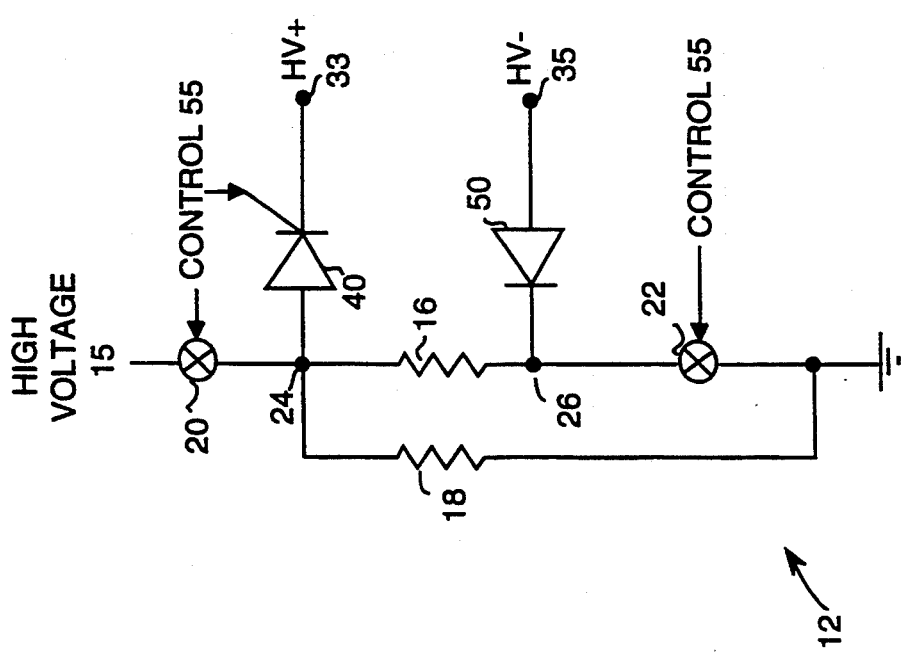

High voltage source 15 of defibrillation output stage circuit 10 according to the invention is preferably a 150 microfarad capacitive source. According to one version of the invention, high voltage source 15 is capacitive and includes first and second series capacitors 15a and 15b having a center tap. The individual output stage subcircuits 12 and 14 are illustrated separately in FIGS. 2a and 2b to show their respective components and connections. As shown in FIG. 1, high voltage source 15 provides a lower voltage level to second subcircuit 14 than to first output stage subcircuit 12, in view of second output stage subcircuit 14 being provided with power from the center tap between capacitors 15a and 15b. This has advantages during actual defibrillation activity with respect to the heart of a patient which are not within the scope of the invention addressed herein.

Output stage subcircuits 12 and 14 include in each case interconnected first and second resistors 16 and 18 and first and second switches 20 and 22, the first resistor 16 being connected between first and second switches 20 and 22. First switch 20 is additionally connected to high voltage source 15. First switch 20 is connected at its low side to both first and second resistors 16 and 18, and second resistor 18 is additionally connected to ground. First switch 20 accordingly has first and second terminals, the first terminal being on the high side and connected to voltage source 15 and the second being connected to resistors 16 and 18. It follows that second resistor 18 shunts the series combination of first resistor 16 and second switch 22 along its path to ground. The parallel network of second resistor 18 leading directly to ground in parallel with first resistor 16 leading to ground through second switch 22 accordingly provides an alternate ground path for high voltage source 15 during its test phase. Further, it provides different equivalent resistances to current from high voltage source 15 depending upon the condition of second switch 22. According to a preferred version of the invention, first and second resistors 16 and 18 are preferably 100 K ohm in resistance. If second switch 22 is open (and first switch 20 is closed), whether intentionally or as a result of failure, the resistance seen by high voltage source 15 will be 100 K ohm. When switch 22 is closed, the effective resistance seen will be only 50 K ohm, with the first and second resistors 16 and 18 being connected in parallel. This modifies the time constant for discharge of capacitive voltage source 15 considerably. The time constant is R*C, with R being the effective resistance seen by high voltage source 15 and C being the capacitance of the high voltage source 15. It is clear that with the capacitance C of the high voltage source 15 remaining constant, and with the effective resistance R being reduced in half by closing switch 22 and connecting first resistor 16 in parallel with second resistor 18, the discharge time period will be reduced by one-half.

The defibrillation output stage circuit 10 of FIG. 1 additionally includes two pairs of first and second circuit nodes 24 and 26 which are connectable to the heart 30 of a patient for defibrillation (but not during test operation) through the appropriate one of first and second defibrillation leads 32 and 34. As can be seen with regard to FIG. 1, first circuit node 24 of output stage subcircuit 12 is connected in a circuit path to defibrillation lead 32, and first circuit node 24 of output stage subcircuit 14 is connected in a circuit path to defibrillation lead 34. Similarly, second circuit node 26 of output stage subcircuit 12 is connected in a circuit path to second defibrillation lead 34, and second circuit node 26 of output stage subcircuit 14 is connected in a circuit path to first defibrillation lead 32. As suggested, each of output stage subcircuits 12 and 14 has its own set of circuit nodes 24 and 26. Herein, first defibrillation lead 32 is connected to a circuit node 33 in the path to first circuit node 24 of output stage subcircuit 12 and in another path to second circuit node 26 of output stage subcircuit 14. Further, a silicon controlled rectifier 40 is connected between first circuit node 24 and circuit node 33 in first output stage subcircuit 12 and another silicon controlled rectifier 40 is connected between first circuit node 24 of output stage subcircuit 14 and circuit node 35. In each case, silicon controlled rectifier 40 is effective for conducting electric current toward the heart 30 when silicon controlled rectifier 40 is in active operation. Further, a diode 50 directed toward ground is connected in first output stage subcircuit 12 between second circuit node 26 and circuit node 35, and another diode 50 directed toward ground is connected in second output stage subcircuit 14 between second circuit node 26 and circuit node 33. In each case, circuit node 24 is effective for supplying a preferably positive voltage charge from voltage source 15 through a respective first switch 20. Concomitantly, circuit node 26 is connected to ground (defined as a selected reference point at the low terminal of voltage source 15) through a respective second switch 22. Actual electrical connection to heart tissue at locations selected for application of defibrillating charges is made at defibrillation electrodes 36 and 38 which are connected to the distal ends of respective first and second defibrillation leads 32 and 34. As can be seen with reference to FIG. 1, a "positive" connection is made to first defibrillation electrode 36 by first output stage subcircuit 12. The connection is considered to be positive with reference to ground as defined above, because when the first output stage subcircuit 12 is connected for defibrillation, it will apply a positive shock to the heart at first defibrillation electrode 36, during the first phase of biphasic defibrillation. Second output stage subcircuit 14 applies a positive defibrillation pulse to second defibrillation electrode 38 during the second phase of biphasic defibrillation. It should be noted that while these connections are made to enable defibrillation, during test operation, the defibrillation electrodes 36 and 38 are electrically isolated from the circuitry of first and second output stage subcircuits 12 and 14, as will be discussed in greater detail below.

Defibrillation output stage circuit 10 additionally includes a control circuit 55 which is effective for providing control signals for opening and closing first and second switches 20 and 22 of each of output stage subcircuits 12 and 14, as well as silicon controlled rectifiers 40 of the subcircuits 12, 14. Silicon controlled rectifiers 40 are well-known switch devices which permit unidirectional current flow. They can be turned on by a suitable control signal from control circuit 55, but they cannot be turned off independently. First and second switches 20, 22 are preferably insulated gate bipolar transistors (IGBT's). IGBT's may be used in defibrillation test circuit 10 in lieu of the silicon controlled rectifiers (SCR's), but the SCR's are preferred, in part because they consume less power. However, as is well known, once an SCR begins to conduct current, it will continue to conduct current. Accordingly, another switch in series with the SCR is required in order to be able to open the SCR and halt the flow of current. Defibrillation output stage circuit 10 of the preferred version provides for this, by placing first switches 20 in series with corresponding ones of SCR's 40. It is further noted that in lieu of IGBT's being employed for the various connections suggested above, field effect transistors (FET's) may be used as well to accomplish the switching objectives indicated.

During normal operation when a patient is subject to delivery of defibrillation therapy, the defibrillation output stage circuit 10 of FIG. 1 can apply biphasic or monophasic defibrillation shocks to the heart 30. The resistive test components of output stage subcircuits 12 and 14 (i.e., resistors 16 and 18) are substantially bypassed during actual patient defibrillation by action of the control circuit 55 closing switches 20 and 22, as well as silicon controlled rectifier 40. This bypassing occurs for each phase of biphasic defibrillation with subcircuits 12 and 14, and as well during monophasic defibrillation undertaken singly with either of subcircuits 12 or 14. Bypassing occurs, because when silicon controlled rectifier 40 passes the defibrillating shock from high voltage source 15, the currents produced will take the path of low resistance through heart 30. According to one phase of biphasic defibrillation or during one version of monophasic defibrillation, the defibrillation current passes from high voltage source 15, through switch 20, through circuit node 24, through silicon controlled rectifier 40, through defibrillation lead 32, through electrodes 36 and 38 and the intervening heart tissue, through defibrillation lead 34, through diode 50, through circuit node 26, and through switch 22 to ground. During such defibrillation action, resistors 16 and 18 are effectively disconnected, because their resistances, either singly or in parallel, are much higher than the resistance of the heart tissue through which the bulk of the current passes.

During testing of the operability of first and second switches 20 and 22 in each of first and second output stage subcircuits 12 and 14, it is desired electrically to isolate the heart 30 from high voltage source 15 and currents flowing in the circuitry of first and second output stage subcircuits 12 and 14. Such electrical isolation may be accomplished in many ways known to one skilled in the art. Among isolation approaches which are considered workable is to use silicon controlled rectifiers. Electrical isolation of the heart 30 is further facilitated by connection of ground directed diodes 50 connected to leads 32 and 34, which prevent the positive flow of electric current through the leads toward either first or second defibrillation electrodes 36 and 38.

Figure 3:
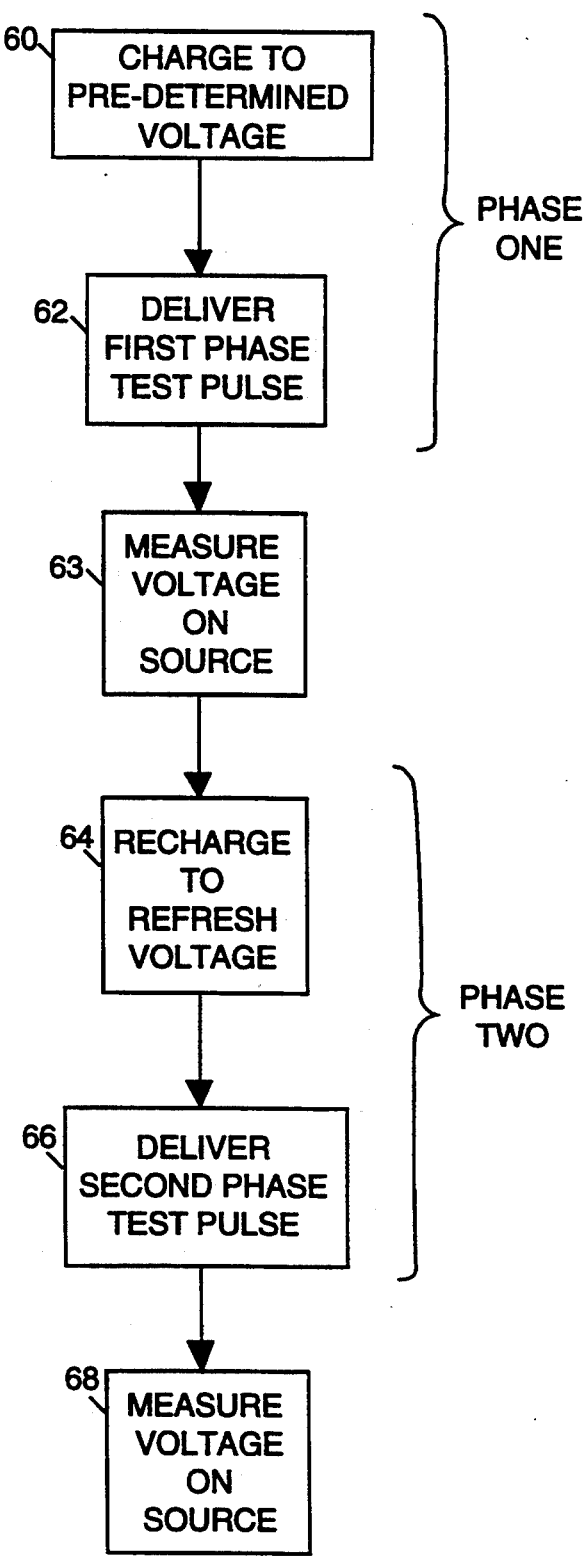
FIG. 3 shows a flow chart of the test method for the output stage test circuit of FIG. 1.

FIG. 3 shows a flow chart of a preferred scheme for testing the components of defibrillation output stage circuit 10 of FIG. 1. According to this approach, testing is accomplished in first and second phases. As shown in FIG. 3, voltage source 15 is first charged to a predetermined voltage level, as indicated at block 60 of FIG. 3. This voltage may for example be 750 volts. The same voltage level is preferably used for testing and actual defibrillation by the implanted defibrillator. Then, according to block 62, a first phase test pulse is delivered. The test pulse delivers no energy to the patient, because of the electrical isolation provided by circuit components such as silicon controlled rectifiers 40 and diodes 50. The test pulse of the first phase of biphasic test is delivered by closing only first and second switches 20 and 22 of the first output stage subcircuit 12.

After the first phase of FIG. 3 has been accomplished, the residual voltage level left on voltage source 15 is measured, in accordance with block 63. One way to accomplish measurement is by connecting the voltage source to a voltage detection arrangement as will be discussed in greater detail below with reference to FIG. 5. As noted, silicon controlled rectifiers 40 and diodes 50 are effective for isolating defibrillation electrodes 36 and 38 during test procedures to ensure that the patient does not experience a shock during testing and verification. Next, according to block 64, voltage source 15 is charged to refresh its voltage level to the previous selected level, e.g. 750 volts. Finally, as indicated at block 66, a second phase test pulse is delivered. This test pulse is delivered by closing only first and second switches 20 and 22 of defibrillation output stage subcircuit 14. After phase two of biphasic test has been accomplished, the level of residual voltage on voltage source 15 is again measured.

The integrity of first and second switches 20 and 22 of respective defibrillation output stage subcircuits 12 and 14 can be judged by the change in high voltage that occurs during the test shock. Testing of a single output stage subcircuit 12, 14 can be accomplished, in accordance with the invention herein. The above test sequence can be initiated by the a clinician, who may initiate the self-test function by an external programming device (not shown) which is well known to those skilled in the art. This is effective for conducting the operation shown in FIG. 3.

Figure 4:
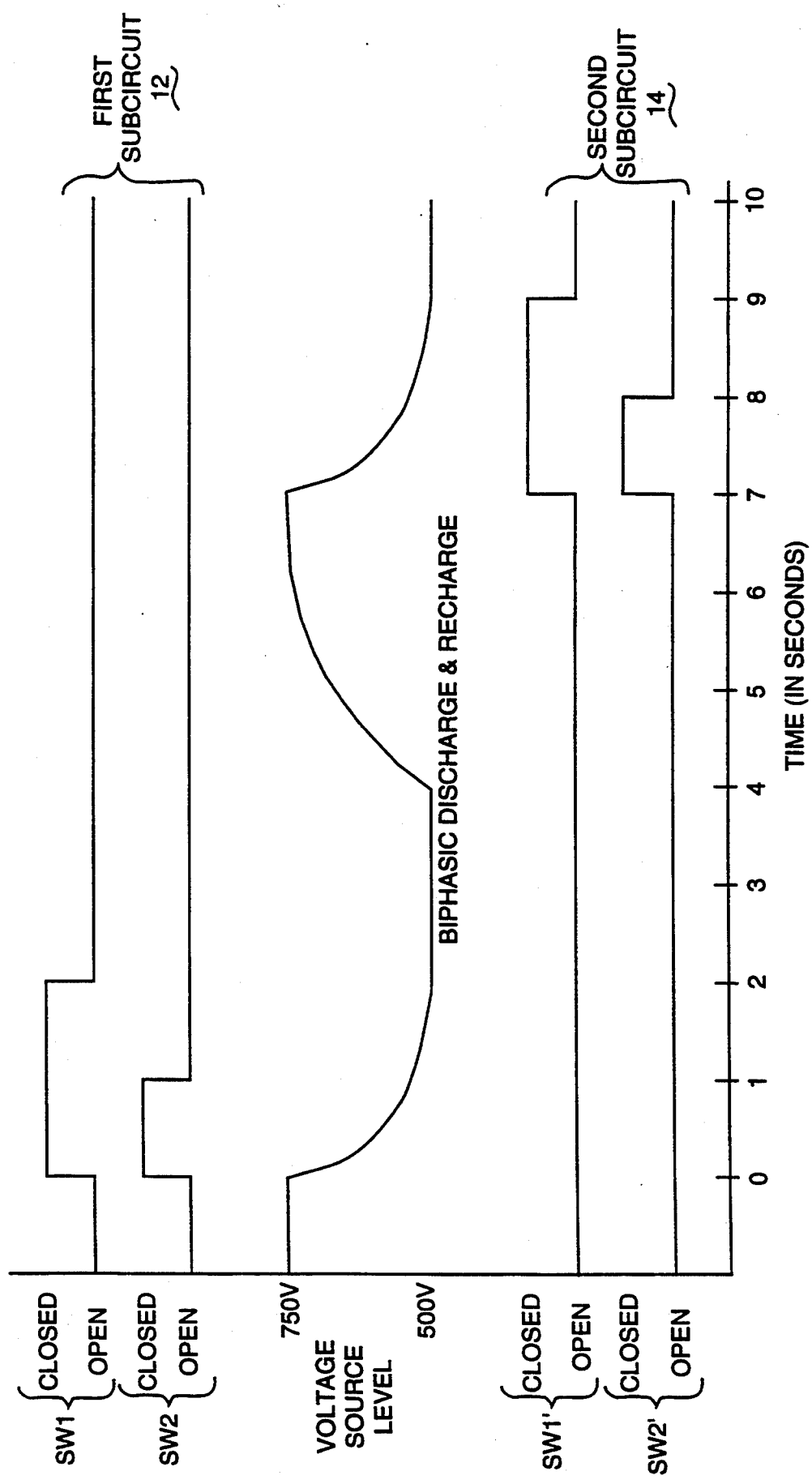
FIG. 4 is a timing diagram which illustrates the sequence of accomplishing the steps of FIG. 3.

FIG. 4 is a timing diagram which illustrates the sequence of accomplishing the steps of FIG. 3. At the top of FIG. 4 first and second traces are shown, indicating high and low states of first and second switches 20 and 22 of first defibrillation output stage subcircuit 12. The high state is considered the closed position for switches 20 and 22, and the low state is considered to be the open position of first and second switches 20 and 22.

At the bottom of the timing diagram of FIG. 4, there are shown additional traces for respective first and second switches 20 and 22 associated with second output stage subcircuit 14. Again, the high state for the indicated traces indicates that the particular switch is closed and allows current to pass therethrough, and the low state indicates an open setting for the particular switch. As can be seen, the closure of respective switches 20 and 22 of the second output stage subcircuit 14 is delayed from the closure time of the first and second switches of first output stage subcircuit 12. The switches of the first phase are closed at time equals zero, while the switches of the second phase are not closed until seven seconds (for example) later. This reflects the progress of test operation first in the first output stage subcircuit 12 and then its continuation with test operation with respect to the second output stage subcircuit 14.

A middle trace in FIG. 4 illustrates the changes in the level of voltage and charge on high voltage source 15 during the progress of biphasic testing. Initially, the voltage level on voltage source 15 may for example be 750 volts. For one second, according to a hypothetical test sequence, both switches of the particular phase are closed, opening parallel paths to ground, and permitting relatively rapid charge dissipation during that second of joint closure. At the end of the second, the second switch is opened. Current can only pass in a single branch; accordingly, for switches in good condition, charge will continue to dissipate exponentially but at a more gradual rate. This is reflected in the two-part dips in the discharge waveforms for voltage source 15 in FIG. 4.

By conducting either the monophasic or biphasic tests indicated above, it can be established whether there are defects of certain kinds present in the first and second switches 20 and 22 of either one or both of output stage subcircuits 12, 14. In particular, if in either phase of the test, one of second switches 22 fails to close, then the voltage drop from capacitive voltage source 15 will be limited to a particular drop, because the current path through second resistor 16 will be unavailable due to failure of second switch 22 to close. With this parallel resistance path unavailable, the only current flow will be through the second resistor 18 which shunts first resistor 16 and second switch 22 to ground, in the case of either first or second output stage subcircuit 12 or 14. If both current paths were available, the combination of parallel resistances 16 and 18 would result in a diminished effective total resistance seen by voltage source 15 and an increased level of discharge to ground over a given period of time. According to one version of the invention in which the predetermined voltage pulse from voltage source 15 is 750 volts, the resultant voltage on the voltage source after discharge of either first or second defibrillation output stage subcircuit 12 or 14 may be 613 volts. With possible failure of second switch 22 to close, leaving only the current path through the first resistor 16 open, the voltage drop during the given time period may result in a measurement of 657 volts. With second switch 22 fused closed, the drop may be 574 volts, for example. With both first and second switches 20 and 22 defectively open, there would be no voltage drop at all, leaving the resultant voltage to be the initial voltage of 750 volts. Fusion of the first switch 20 is determinable by opening first switch 20 and waiting a predetermined amount of time to determined whether there was a voltage drop attributable to continued charge leakage from voltage source 15 after the current flow ought to have ceased. According to this example, post test voltage measurement results can be used to distinguish a functioning defibrillator circuit from a damaged one. These results can automatically be displayed on a programing device screen, as would be understood by one skilled in the art.

Figure 5:
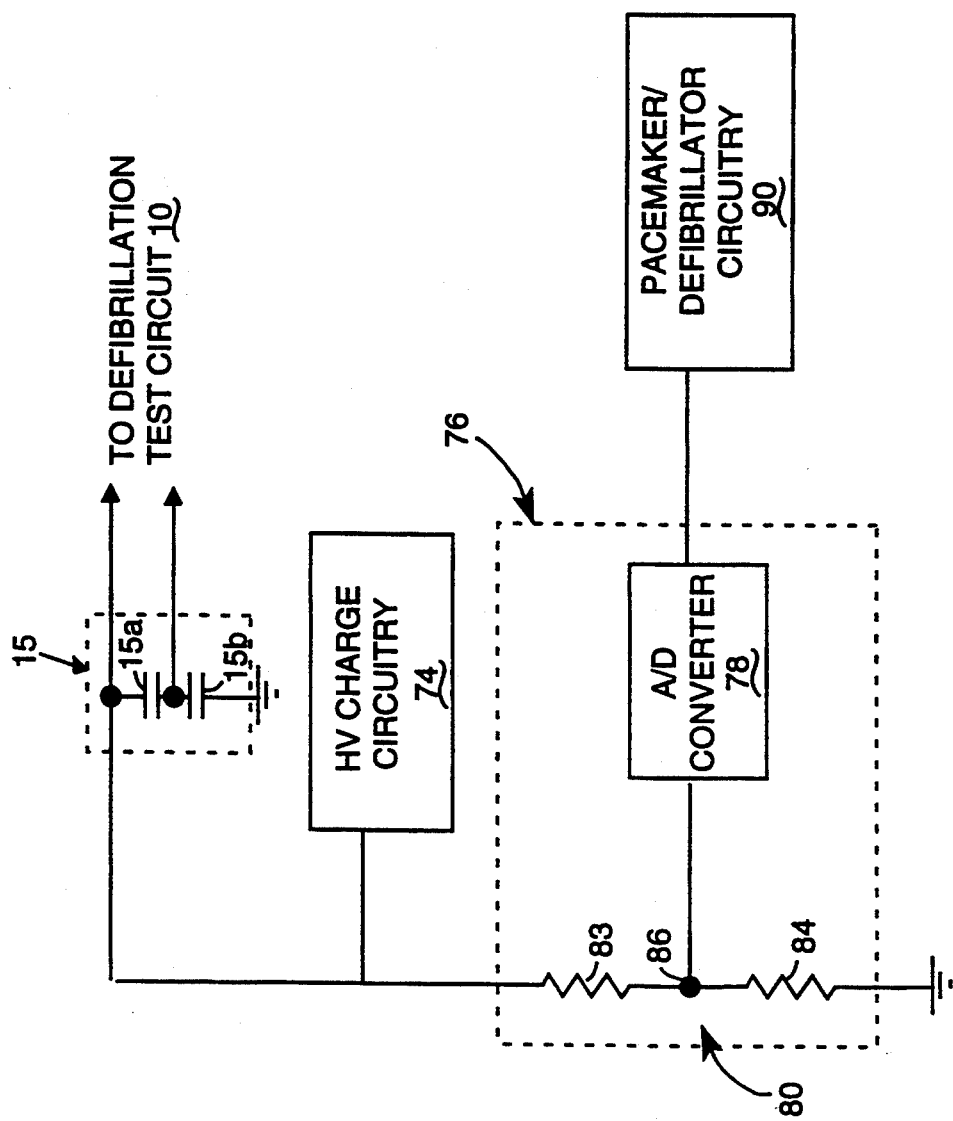
FIG. 5 shows an electric circuit for charging and measuring the potential on the voltage source incident to test operation.

FIG. 5 shows details of electric circuitry for charging voltage source 15 and measuring the potential on voltage source 15 during discharge and test operation. In particular, according to one version, voltage source 15 includes first and second series capacitors 15a and 15b. Voltage source 15 is connected to high voltage charge circuitry 74 and measurement circuitry 76, which respectively permit voltage source 15 to be charged to a selected voltage level and to have its potential measured during discharge. Measurement circuitry 76 may include an analog to digital converter 78 and a voltage divider circuit 80 including first and second series resistors 83 and 84 which are connected at a central node 86. Resistor 84 is preferably much smaller than resistor 83 in resistance, permitting the analog to digital converter 78 to measure a scaled down portion of the full charge voltage on voltage source 15. The digital measurement output of analog to digital converter 78 is provided to well-known pacemaker/defibrillator circuitry 90 for storage or further transcutaneous transmission out of the body of the patient having the implanted device. If the voltages measured indicate that any switches for applying defibrillating pulses to the patient from the implanted defibrillator are defective, the device may have to be replaced.

While this invention has been described in terms of several preferred embodiments, it is contemplated that many alterations, permutations, and equivalents will be apparent to those skilled in the art. It is therefore intended that the following appended claims be interpreted as including all such alterations, permutations, and equivalents as fall within the true spirit and scope of the present invention.

What is claimed is:

1. A circuit for testing an output stage of an implantable defibrillator system including at least first and second defibrillation electrodes coupled to said output stage, said circuit comprising:
   (a) voltage means for supplying electric current,
   (b) first switch means for controlling electric current conduction from said voltage means, said first switch means having open and closed states,
   (c) circuit means for electrically conducting electric current from said voltage means to ground through said first switch means when said first switch means is in a closed state, said circuit means being effective for conducting different current levels depending upon the state of said first switch means, and
   (d) means for electrically isolating said voltage means from said defibrillation electrodes for applying electric defibrillation shocks to a patient, whereby a condition of said first switch means is electrically determinable without risk of electric shock to a patient having the implanted defibrillator.

2. The circuit according to claim 1, wherein said circuit means comprises first and second resistors connected in parallel.

3. The circuit according to claim 1, wherein said circuit means includes first and second subcircuits connected in parallel.

4. The circuit according to claim 2, wherein said circuit means further comprises second switch means for controlling said current conduction from said voltage means, said second switch means being effective for operating in open and closed states, and said second switch means and said first resistor being connected in series.

5. The circuit according to claim 1, wherein said voltage means is capacitive.

6. A test circuit for testing an output stage of an implantable defibrillator system including at least first and second defibrillation electrodes coupled to said output stage, the test circuit comprising:
   (a) a voltage source effective for producing a predetermined electric charge,
   (b) first and second switch means for controlling electric current conduction from said voltage source, said first and second switch means being connected in series between a ground contact and said voltage source,
   (c) first and second resistive means for conducting electric current, said first resistive means being connected in series between said first and second switch means, and said second resistive means being connected in parallel with said first resistive means and said second switch means, and
   (d) means for electrically isolating said voltage source from said defibrillation electrodes for applying electric defibrillation charges to a patient, whereby said first and second switch means are testable without risk of shock to a patient having the implanted defibrillator.

7. The test circuit of claim 6, further comprising control means for controlling application of electric charge for test purposes through said first and second switch means.

8. The test circuit of claim 6, wherein at least one of said first and second switch means is an insulated gate bipolar transistor.

9. The test circuit of claim 6, wherein said means for electrically isolating includes a silicon controlled rectifier.

10. The test circuit of claim 6, further comprising third and fourth switch means for controlling electric current conduction from said voltage source, said third and fourth switch means being connected in series to ground, and said third switch means being connected to said voltage source.

11. The test circuit of claim 10, further comprising third and fourth resistive means for passing currents to ground, said third resistive means being connected between said third and fourth switch means and said fourth resistive means being connected between said third switch means and ground.

12. The test circuit of claim 11, wherein said fourth resistive means is connected in parallel with said third resistive means and said fourth switch means.

13. A test method for enabling evaluation of an operability and status of a defibrillator switch in an implantable defibrillator, said method comprising:
  (a) establishing charge and ground connections to first and second nodes for supplying charge currents to a patient for defibrillation,
  (b) connecting a switch to a source of defibrillating charge,
  (c) connecting a resistor to first and second nodes and to said switch, such that said resistor is connected to said switch on one side and that said first resistor is connected to said second node at its other end,
  (d) electrically isolating said first and second nodes to prevent shocking a patient, and
  (e) closing said switch to enable electrical measurements to be made indicative of a level of flow of electric current through said resistor.

14. A method of enabling testing of switches connecting charge and ground connections to first and second nodes effective for supplying defibrillating charges to the heart of a patient, said method comprising:
  (a) connecting first and second circuits each including first and second switches connected in series, and connecting each of said first switches to a source of defibrillating charge,
  (b) connecting a first resistor between the first and second switches in each circuit, and a second resistor in parallel with the first resistor and the second switch of each circuit,
  (c) electrically isolating said first and second nodes to prevent shock to a patient, and
  (d) closing said first and second switches to enable electrical measurements to be made indicative of a level of flow of electric current through said first and second resistors.

15. The method according to claim 14, further comprising electrically isolating said first and second circuits from said patient with respective first and second silicon controlled rectifiers.

16. The method according to claim 14, further comprising the step of taking a measurement of an electric charge remaining in said voltage source at a predetermined time after discharge of said voltage source through one of said first switches.

17. A biphasic implantable defibrillator output stage test circuit comprising:
  (a) a voltage source effective for producing a predetermined electric charge,
  (b) first and second pairs of electric switches for controlling electric current conduction from said voltage source, said first and second pairs each including first and second switches connected in series between ground and said voltage source,
  (c) first and second pairs of resistors, each of said pairs of resistors including first and second resistors connected in parallel, the second resistor of each pair of resistors being connected in series with the second switch of the corresponding one of said first and second pairs of electric switches, and
  (d) means for selectively electrically isolating said voltage source and said first and second pairs of switches and resistors from a patient during test operation, to protect the patient from electric shock.

18. The biphasic implantable defibrillator output stage test circuit of claim 17, including means for controlling opening and closing of said first and second switches of said first and second pairs of switches.

19. The biphasic implantable defibrillator output stage test circuit according to claim 17, comprising means for measuring a level of said voltage source at a predetermined time after discharge.

20. An implantable defibrillator system for delivering defibrillation shocks to a patient's heart comprising:
  a high voltage source;
  means for charging said high voltage source;
  a plurality of electric leads for delivering said defibrillation shocks from said high voltage source to said patient's heart;
  an output stage coupled between said high voltage source and said plurality of electrical leads, including a plurality of high voltage output switches;
  a control circuit for controlling operation of said high voltage switches; and
  test circuit means for testing an integrity of said plurality of high voltage output switches.

* * * * *